US00PP32451P2

(12) United States Plant Patent
van Noort

(10) Patent No.: US PP32,451 P2
(45) Date of Patent: Nov. 10, 2020

(54) ***ECHINACEA* PLANT NAMED 'NOECTHREE'**

(50) Latin Name: ***Echinacea* hybrid**
Varietal Denomination: Noecthree

(71) Applicant: Marco van Noort, Warmond (NL)

(72) Inventor: Marco van Noort, Warmond (NL)

(73) Assignee: MARCO VAN NOORT BREEDING, BV, Warmond (NL)

( * ) Notice: Subject to any disclaimer, the term of this patent is extended or adjusted under 35 U.S.C. 154(b) by 0 days.

(21) Appl. No.: 16/602,950

(22) Filed: Dec. 31, 2019

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 6/1448; A01H 5/02
See application file for complete search history.

*Primary Examiner* — Keith O. Robinson
(74) *Attorney, Agent, or Firm* — Penny J. Aguirre

(57) ABSTRACT

A new cultivar of *Echinacea* plant named 'Noecthree' that is characterized by its short plant height and a compact plant habit, its anemone type (semi-double) inflorescences, its inflorescences that are large in size and white in color, its strong stems, and its floriferous blooming habit.

2 Drawing Sheets

Botanical classification: *Echinacea* hybrid.
Variety denomination: 'Noecthree'.

CROSS REFERENCE TO A RELATED APPLICATION

This application is related to a European plant breeders' rights application filed on Sep. 6, 2017, application No. 2017/2146. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Echinacea* of hybrid origin and will be referred to hereafter by its cultivar name, 'Noecthree'. 'Noecthree' represents a new cultivar of coneflower, an herbaceous perennial grown for landscape use.

The new cultivar arose from an ongoing breeding program of the Inventor's in Warmond, The Netherlands. The objective of the breeding program was to develop a new cultivar *Echinacea* with semi-double flowers (anemone type) combined with a strong and floriferous plant habit. The new cultivar arose from a cross made in July of 2014 between *Echinacea* 'Noortdeli' (not patented) as the female parent and an unnamed and unpatented proprietary plant from the Inventor's breeding program as the male parent. 'Noecthree' was selected as a single unique plant from the resulting seedlings in July of 2016.

Asexual propagation of the new cultivar was first accomplished by division in Warmond, The Netherlands in November of 2016 under the direction of the Inventor. Asexual propagation by division and tissue culture using meristematic tissue has determined that the characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Noecthree' as a unique cultivar of *Echinacea.*

1. 'Noecthree' exhibits a short plant height and a compact plant habit.
2. 'Noecthree' exhibits anemone type (semi-double) inflorescences.
3. 'Noecthree' exhibits inflorescences that are large in size and white in color.
4. 'Noecthree' exhibits strong stems.
5. 'Noecthree' exhibits a floriferous blooming habit.

The seed parent differs from 'Noecthree' in having inflorescences that are purple-red in color. The pollen parent differs from 'Noecthree' in having a much taller plant height. The new cultivar can be most closely compared to the cultivars 'White Double Delight' (U.S. Plant Pat. No. 23,472) and 'Milkshake' (U.S. Plant Pat. No. 20,594). 'White Double Delight' is similar to 'Noecthree' in inflorescence color and shape. 'White Double Delight' differs from 'Noecthree' in having a much taller plant height. 'Milkshake' is similar to 'Noecthree' in inflorescence shape. 'Milkshake' differs from 'Noecthree' in inflorescences that are smaller in size and stems that are weaker in strength.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1). Disclosures include but may not be limited to website listings by press organizations; Plantkeuze, The National Garden Database, Horticulture Connected, and KVBC and Horticulture Week that published the listing of the new cultivar entry into the new plant competition at Plantarium, in August 2018 with no offers for sale and a listing by Esveld that included in their list as a future plant, but had no plant material available.

BRIEF DESCRIPTION OF THE DRAWINGS

The plants in the accompanying photographs depict the characteristics of a one-year-old plant of 'Noecthree' as grown in a 17-cm container in Warmond, The Netherlands.

The photograph in FIG. 1 provides a side view of 'Noecthree' in bloom.

Figure 1:
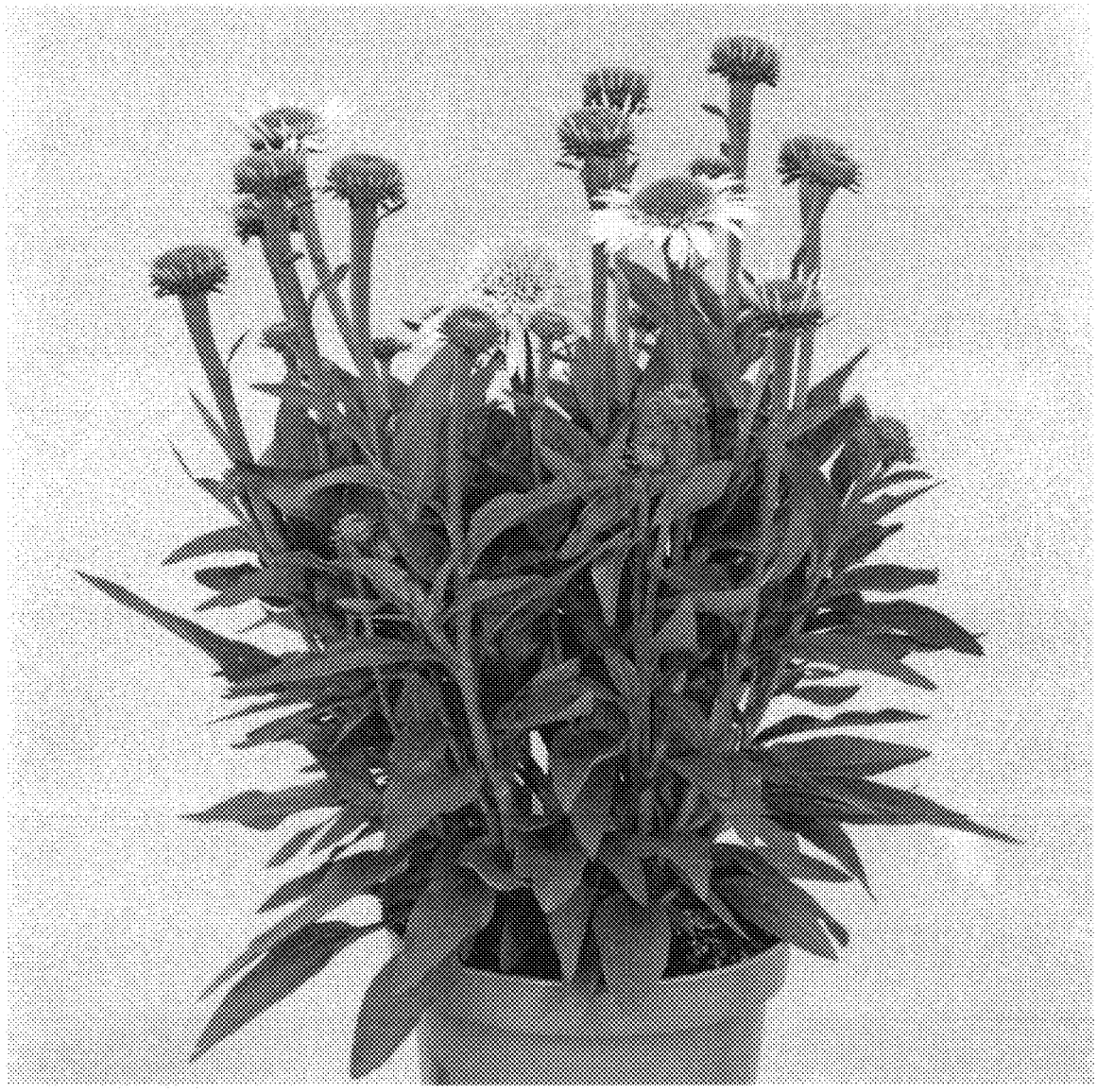
Figure 2:
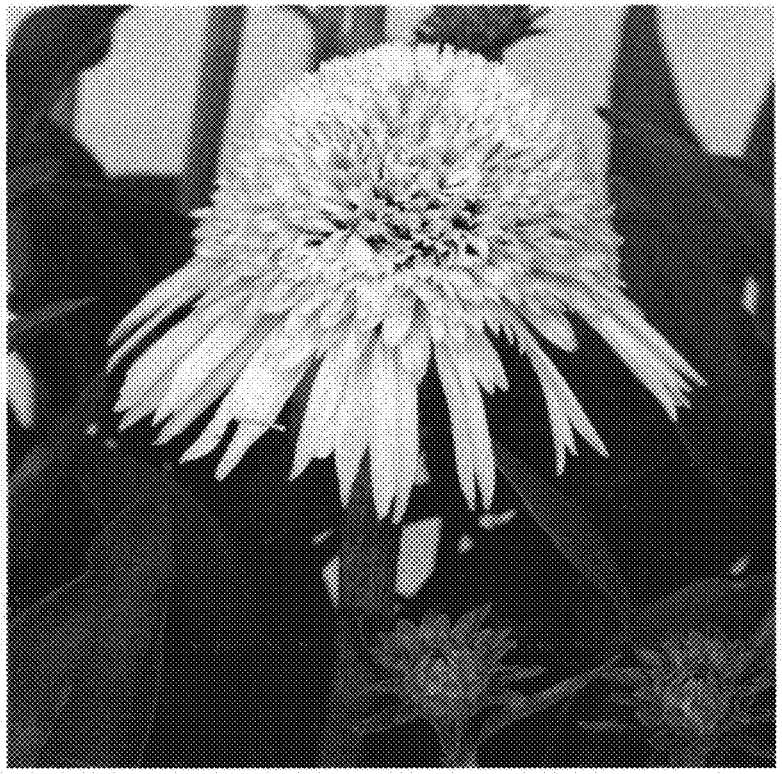

The photograph in FIG. 2 provides a close-up view of an inflorescences of 'Noecthree'.

Figure 3:
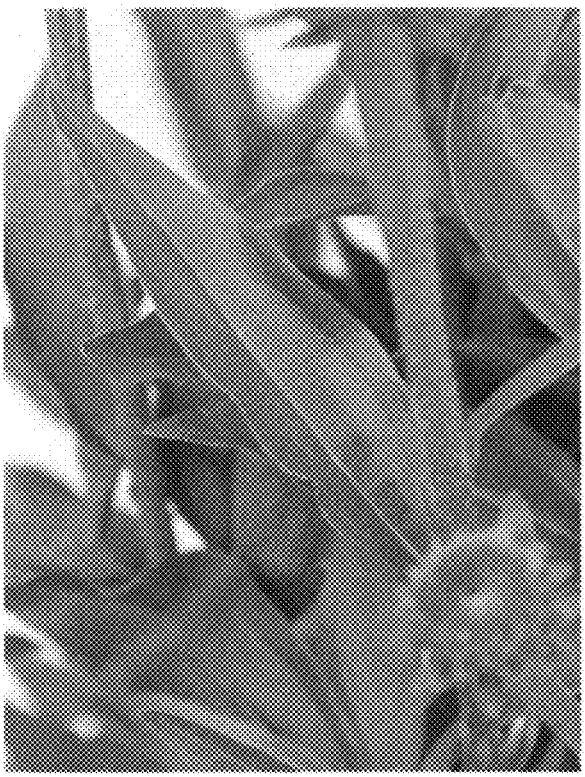

The photograph in FIG. 3 provides a close-up view of the foliage of 'Noecthree'.

The colors in the photograph may differ slightly from the color values cited in the detailed botanical description, which accurately describe the colors of the new *Echinacea*.

BOTANICAL DESCRIPTION OF THE PLANT

The following is a detailed description of one-year-old plants of the new cultivar as grown outdoors in 17-cm containers in Warmond, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Approximately 6 weeks from midsummer into fall in The Netherlands.

*Plant type*.—Herbaceous perennial,

*Plant habit*.—Clump forming, compact and short with upright and strong stems.

*Height and spread*.—Average of 27.9 cm from soil level to top of foliar plane, 37.8 cm from soil level to top of floral plane, 37.2 cm in spread as grown in a 17-cm container, reaches an average of 50 cm in height and 45 cm in width as a mature plant in the landscape.

*Cold hardiness*.—At least to U.S.D.A. Zone 3.

*Diseases and pests*.—No resistance or susceptibility to pests or diseases has been observed.

*Root description*.—Fibrous.

*Propagation*.—Tissue culture and division.

*Root development*.—An average of 30 days for root initiation with a finished plant produced in about 3 months.

*Growth rate*.—Moderately vigorous.

Stem description:

*Shape*.—Rounded.

*Stem color*.—144A.

*Stem size*.—Average of 6 mm in diameter and an average of 18.9 cm in length.

*Stem surface*.—Rough to the touch, moderately covered with short strigose hairs; 0.5 mm in length, NN155D in color.

*Stem strength*.—Strong.

*Stem aspect*.—Stems grow in an average angle of 15° from the base (0°=vertical).

*Branching*.—Main flowering stems grow from the base with a few lateral branches present, average of 4 primary branches, 5 lateral branches per primary stem.

Foliage description:

*Leaf shape*.—Ovate to narrowly ovate.

*Leaf division*.—Simple.

*Leaf base*.—Attenuate.

*Leaf apex*.—Acute.

*Leaf venation*.—Pinnate, upper surface; 144B to 144C, lower surface; 145A to 145B.

*Leaf margins*.—Entire, slightly undulate.

*Leaf attachment*.—Petiolate.

*Leaf arrangement*.—Alternate.

*Internode length*.—An average of 3.6 cm.

*Leaf size*.—Average of 9.1 cm in length and 3.3 cm in width.

*Leaf color*.—Young upper surface; 143A, young lower surface; 146B, mature upper surface; NN137A, mature lower surface; NN137D.

*Leaf surface*.—Both surfaces are matte, non-rugose, rough to the touch and moderately covered with very short strigose hairs; average length of 0.3 mm and 156D in color.

*Petioles*.—Basal leaves average of 6.8 cm in length and 2 mm in diameter, stem leaves an average of 1.9 cm in length and 4 mm in diameter, moderately covered with very short strigose hairs 0.3 mm in length and 156D in color, color; young upper surface 143A, young lower surface 146B, mature upper surface NN137A, mature lower surface NN137D.

Flower description:

*Type*.—Terminal capitulum, heterogamous with ray florets around the head margin and anemone-type disk florets in the center.

*Capitulum number*.—Two terminal capitulum per main stem and lateral branches.

*Lastingness of inflorescence*.—About 10 days.

*Capitulum size*.—Matures to about 4.5 cm in height and 8.1 cm in diameter, disk size is an average of 5.4 cm in diameter.

*Fragrance*.—None.

*Involucral bracts or phyllary*.—Average of 80 arranged in 3 overlapping rows, up to 7 mm in length and 3 mm in width, broad cuneate base, acute apex, ovate in shape, entire margins moderately covered with short hairs 0.3 mm in length and 156D in color, upper surface; smooth, slightly glossy and 137C in color, lower surface smooth, slightly glossy and NN137B to NN137C in color.

*Buds*.—Flattened globular in shape, up to 3.5 cm in diameter and 1.8 cm in length, color; 144A, immature ray florets 145C, changing to 145D at the base.

*Peduncle*.—Strong, straight on top of main (flowering) stem, average angle of third peduncle 35° (0°=straight upright), terminal peduncle length is 11.3 cm, diameter of peduncle is 6.5 mm, third peduncle length is 12 cm, diameter is 5 mm, 144A in color, surface is slightly glossy and covered with short strigose hairs, 0.3 mm in length and too small to measure color.

*Ray florets*.—Rotate, average of 23, whorled, oblanceolate in shape, average of 3.6 cm in length and 8.5 mm in width, deeply praemorse to cleft apex, attenuate base, entire margin, moderately drooping in an average angle of −40°, upper and lower surface texture is smooth, velvety and glabrous, color: when opening upper and lower surface; 157C, 157B at the tip, when fully open upper surface; 157B, when fully opened lower surface; 150D, tip 145B.

*Disk flowers* (*bisexual*).—Numerous, average of 370, narrowly oblong in shape, 85% of all petals are fused, arranged spirally on disc average of 13 rows, average of 1.8 cm in length and 5 mm in width, entire margin, both surfaces smooth, dull and slightly velvety in appearance, color: upper and lower surface when opening; 157C, mid-section to tip 157B, upper and lower surfaces when fully opened; 144B, mid-section to tip between 150D and 157C.

*Receptacle*.—Globular in shape, average of 1.1 cm in diameter and 9 mm in height, 155C in color.

*Receptacle spines*.—Acicular in shape, acute apex, attenuate base, 1.2 cm in length, 2 mm in diameter, smooth and glossy surface, color: apex; 13A, mid-section; 143A, base; 145D.

Reproductive organs:

*Gynoecium*.—Pistil; 1 (only present in disc florets), 8 mm in length, stigma; decurrent, reflexed, 1 mm in length, 2 mm in diameter, N144B, style; 6 mm in length and 145C in color, ovary; 157D in color.

*Androecium*.—Stamens; 5, filament 3 mm in length and 145D in color, anther; basifixed, linear in shape, 3 mm in length and N200A in color, pollen; moderate in quantity, 14A in color.

*Fruit/seed*.—No fruit or seed detected to date.

It is claimed:

1. A new and distinct cultivar of *Echinacea* plant named 'Noecthree' substantially as herein illustrated and described.

* * * * *